United States Patent [19]

Stephens et al.

[11] 4,372,150

[45] Feb. 8, 1983

[54] FLOW MONITORING METHOD AND APPARATUS

[75] Inventors: Donald E. Stephens, Palo Alto; Robert J. Ehret, Los Altos, both of Calif.

[73] Assignee: Beckman Instruments, Inc., Fullerton, Calif.

[21] Appl. No.: 156,718

[22] Filed: Jun. 5, 1980

[51] Int. Cl.³ ............................................. G01M 3/28
[52] U.S. Cl. .............................. 73/40.5 R; 73/61.1 C; 340/608
[58] Field of Search ................ 73/61.1 C, 40.5 R; 210/198.2; 422/70, 81; 340/606, 608, 609; 417/300, 9; 137/487.5; 128/214 E

[56] References Cited

U.S. PATENT DOCUMENTS

| Re. 29,454 | 10/1977 | Ashmead et al. | 222/1 |
|---|---|---|---|
| 3,690,150 | 9/1972 | Mullen | 73/40.5 |
| 3,695,094 | 10/1972 | Holme | 73/40.5 |
| 3,711,689 | 1/1973 | Park | 235/151.34 |
| 3,736,930 | 6/1973 | Georgi | 128/214 E |
| 3,756,456 | 9/1973 | Georgi | 222/1 |
| 3,817,658 | 6/1974 | Murase | 417/2 |
| 3,820,395 | 6/1974 | Hartwell | 73/231 |
| 3,855,480 | 12/1974 | Striker et al. | 307/149 |
| 3,871,229 | 3/1975 | Fletcher | 73/204 |
| 3,890,968 | 6/1975 | Pierce et al. | 128/214 E |
| 3,976,400 | 8/1976 | Major | 417/248 |
| 3,985,021 | 10/1976 | Achener et al. | 73/61.1 |
| 4,001,801 | 1/1977 | Moulet | 340/239 R |
| 4,018,685 | 4/1977 | Saunders et al. | 210/141 |
| 4,019,652 | 4/1977 | Suh et al. | 222/1 |
| 4,037,598 | 7/1977 | Georgi | 128/214 E |
| 4,063,077 | 12/1977 | Wright | 364/502 |
| 4,066,879 | 1/1978 | Leaver et al. | 364/498 |
| 4,105,028 | 8/1978 | Sadlier et al. | 128/214 E |
| 4,155,683 | 5/1979 | Mochizuki et al. | 417/269 |
| 4,186,769 | 2/1980 | Buyce | 137/566 |
| 4,200,203 | 4/1980 | Rider | 222/14 |
| 4,233,156 | 11/1980 | Tsukada | 73/61.1 C |

Primary Examiner—S. Clement Swisher
Attorney, Agent, or Firm—R. J. Steinmeyer; F. L. Mehlhoff; T. R. Schulte

[57] ABSTRACT

A method and apparatus for monitoring flow rate through a conduit. A flow number indicative of the flow rate of a liquid through the conduit is compared with a preselected reference number. The actual liquid flow through the conduit provides a clocking signal which determines the time span during which a count signal, indicative of the intended flow rate into the conduit, is accumulated thereby providing the flow number.

5 Claims, 3 Drawing Figures

FLOW MONITORING METHOD AND APPARATUS

BACKGROUND OF THE INVENTION

1. Field of the Invention

The invention relates to the field of instrumentation control where the operation of the instrument depends upon liquid flow rate. More particularly, the invention relates to flow monitoring in liquid chromatographic apparatus. By way of further characterization but not by way of limitation thereto, the invention is an apparatus for monitoring the flow of the eluent/reagent mixture in a liquid chromatography apparatus and turning off the apparatus if flow rates fall outside predetermined operating parameters.

2. Description of the Related Art

An amino acid analyzer is a specialized application of a liquid column chromatographic separation technique which utilizes ion exchange resin as the stationary phase, with eluting buffers of varying pH and salt concentration employed as the moving phase. Amino acids contained in a sample introduced onto the top of the column are separated from each other as they are eluted through the resin bed which comprises the column packing. For amino acid analysis, the method of choice for detecting the amino acids in the effluent stream has been to combine the column effluent with a reagent which is metered into the stream at a flow rate which is proportional to that of the column eluent. The reagent, upon combining with amino acids present in the stream, forms compounds which, when subjected to a further development process, can be detected by specific changes in optical properties.

An amino acid analyzer may be automated such that samples are automatically injected into the column in a cyclic manner. The physical parameters (flow rates, temperature) of each analysis are repeated with close precision for each sample. It is important that the flow rate of the eluting buffer remain constant during an analysis and that the metering ratio of column effluent and reagent be constant. In addition, especially during periods of unattended automatic operation, it is important that the flow rate of the analyzer be monitored and the analyzer shut down if flow conditions move outside of specified tolerances.

Prior devices require the operator to adjust the flow rates by individually adjusting the pump stroke displacement of each of the pumps, a laborious and time consuming process. In addition, existing flow monitor devices require painstaking adjustment for each flow rate selected. These adjustments require a certain level of intuitive skill not attained by all operators, hence the systems malfunction. That is, the operator adjusts the flow monitor reference point while the analyzer is operating normally such that a warning light would just go on. He would then back off the adjustment until the warning light goes out. The sensitivity thus achieved is such that any small change in flow rate could trigger the warning light. The intuitive skill required comes from knowing how much to adjust the reference point such that the warning light will go on when the flow rate drops to an unsafe level, yet not adjust the reference point so close that a small transient in flow rate will trigger the alarm.

SUMMARY OF THE INVENTION

The invention is in a liquid flow rate monitoring apparatus and method which compares a flow number, representative of a count signal as accumulated for a time determined by a clock signal propagated by the actual liquid flow rate being monitored, with a preselected reference number. The count signal is propagated in response to the intended rate of introduction of a liquid into a conduit by an introducing means. A generating means produces the clocking signal in response to the actual flow of the liquid through or from the conduit. A comparing means compares the flow number with the preselected reference number.

The introducing means includes a means for pumping a liquid into the conduit and a means for controlling the pumping means. The controlling means includes a frequency synthesizer associated with the pumping means. The controlling means also includes a logic gate connected to the frequency synthesizer, a programmer circuit connected to the logic gate, a power supply connected to the frequency synthesizer, and an adjustable reference voltage connected to the power supply. The reference voltage controls the intended liquid flow rate into the conduit and may be varied in accordance with the desires of the operator.

The count signal is propagated by a voltage controlled oscillator which is operatively associated with the controlling means. The count signal produced by the voltage controlled oscillator is directly proportional to the intended rate of introduction of liquid into the conduit. The count signal is fed to a binary counter and accumulated for a period determined by the clocking signal thereby generating a flow number. The resulting flow number is then fed to the comparing means. The clock signal, in the preferred embodiment, is generated by a drop detector associated with the output flow of the liquid from the conduit. The clocking signal is fed to the binary counter to determine the time frame during which the count signal is accumulated to produce the flow number. If the flow number exceeds the preselected reference number to indicate low flow then a shutdown pulse may be generated to turn off the system.

DESCRIPTION OF THE PREFERRED EMBODIMENT

Figure 1:
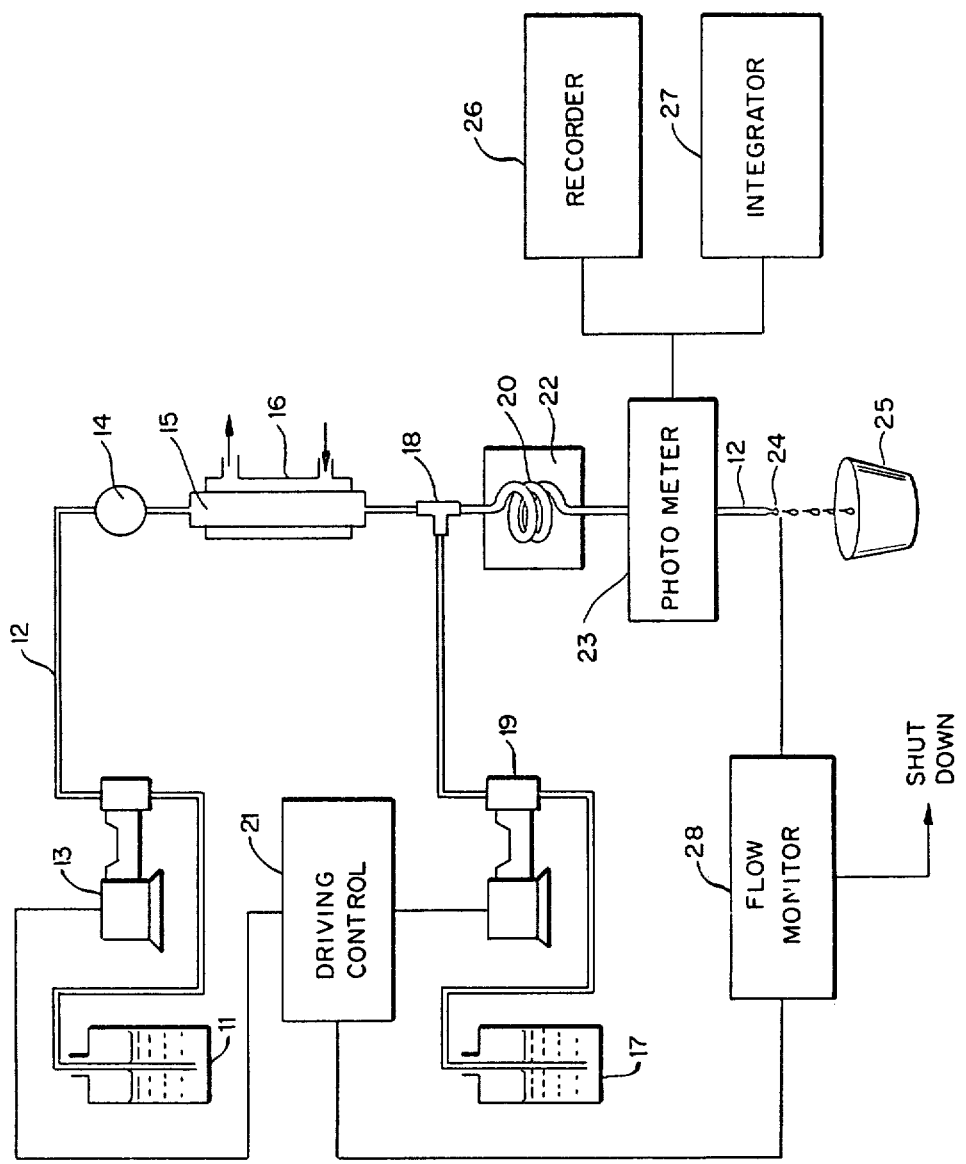
FIG. 1 is a schematic of the flow system.

Like reference numerals denote like structure throughout each of the various figures.

Referring to FIG. 1, a buffer solution 11 is introduced into a conduit 12 by a pump 13. Buffer 11 is combined with a sample to be analyzed at a sample injector 14. The sample plus buffer solution is conducted to a chromatographic column 15. Column 15 is encased in a water jacket 16. The buffer and sample eluent emerges from column 15 and is combined with a reagent solution 17 at a mixing tee 18. Reagent 17 is introduced to mixing tee 18 by a pump 19. Pump 19 and pump 13 comprise a pumping means and are connected to a controlling means 21. The reagent/eluent solution is conveyed from mixing tee 18 to a capillary coil 20. Capillary coil 20 is contained in a heated reactor 22. The reagent/eluent mixture, after traveling through capillary coil 20, moves through a photometer 23 and then through a drop detector 24 to a waste collector 25. A recorder 26 and an integrator 27 are connected to photometer 23. A flow monitor 28 is connected to controlling means 21 and drop detector 24.

Figure 2:
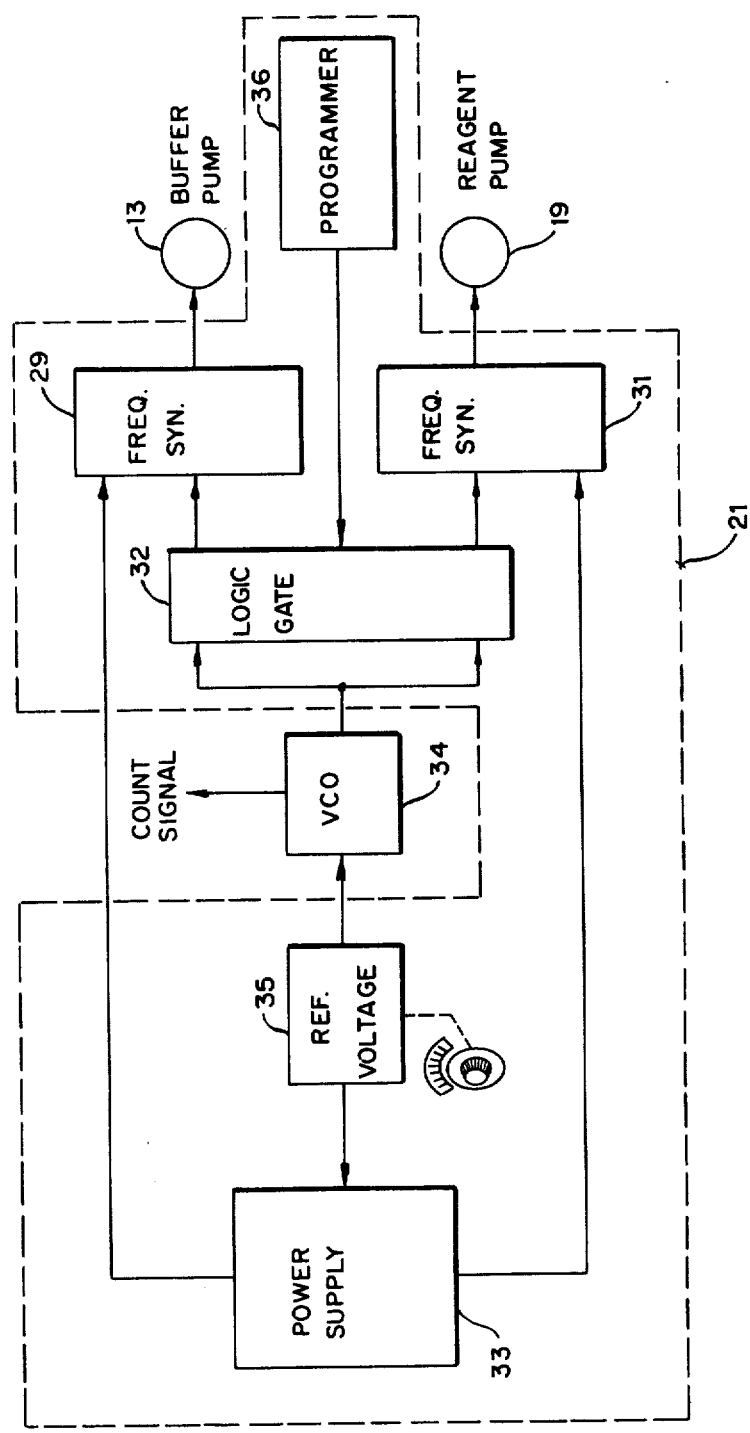
FIG. 2 is a schematic of the pump drive control.

Referring to FIG. 2, the pump controlling means 21 is shown. Buffer pump 13 and reagent pump 19 are connected to a frequency synthesizer 29 and a frequency synthesizer 31, respectively. A logic gate 32 is connected to frequency synthesizers 29 and 31. A power supply 33 is also connected to frequency synthesizers 29 and 31. A voltage controlled oscillator 34 is connected to logic gate 32. An adjustable reference voltage 35 is connected to power supply 33 and voltage controlled oscillator 34. An analyzer programmer circuit 36 is connected to logic gate 32.

Figure 3:
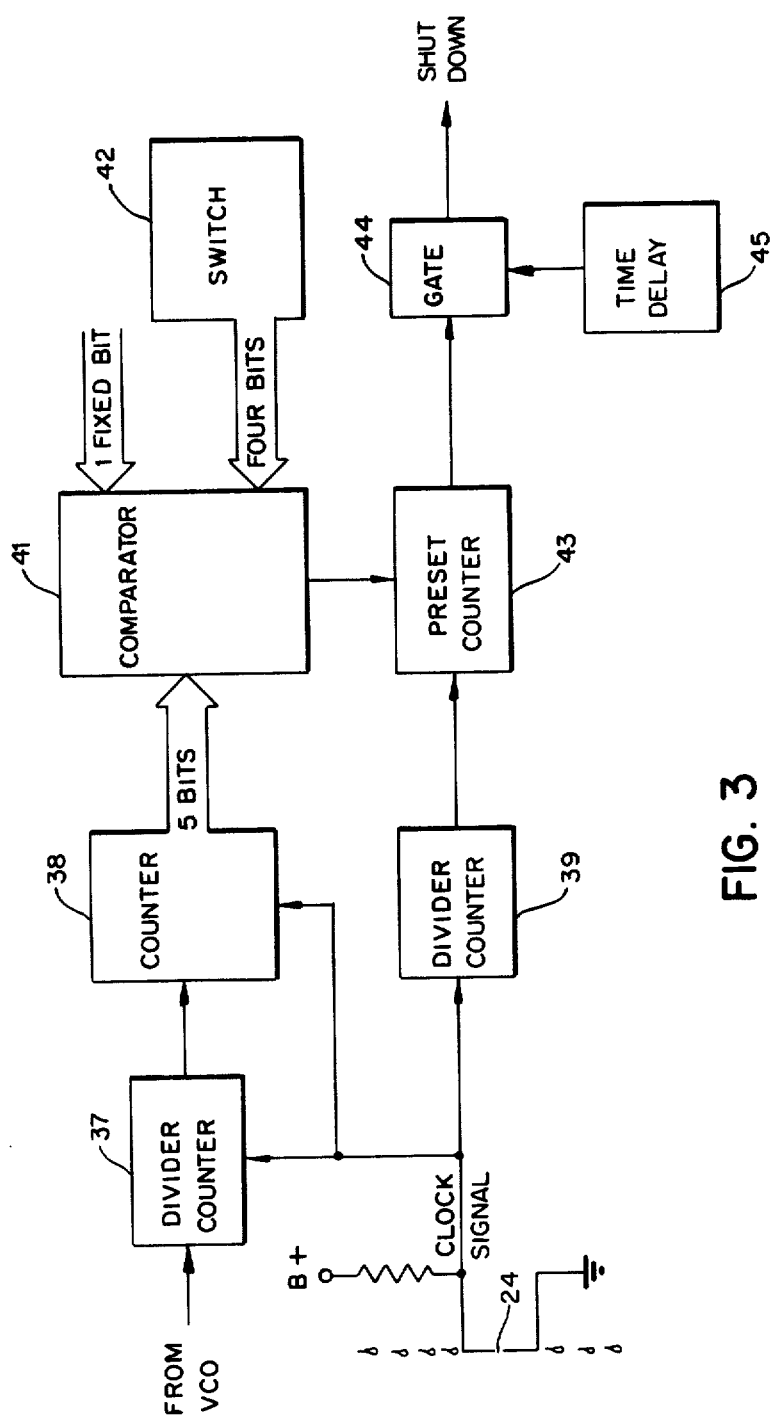
FIG. 3 is a schematic of the flow monitor.

Referring to FIG. 3, flow monitor 28 is shown in detail. A divider counter 37 is connected to voltage controlled oscillator 34 (shown in FIG. 2). Divider counter 37 is connected to a counter 38 and a divider counter 39. A drop detector which includes a conductivity probe 24 is connected to divider counter 37, counter 38 and divider counter 39. Counter 38 is connected to a comparator 41. A binary switch 42 is also connected to comparator 41. A preset counter 43 is connected to divider counter 39, comparator 41, and a gate 44. A time delay circuit 45 is also connected to gate 44.

Mode of Operation

Referring to FIG. 1, both pump 13 and pump 19 are fixed stroke positive displacement reciprocating pumps. These pumps are driven at synchronous speed by controlling means 21. The stroke of reagent pump 19 is usually set at one half that of buffer pump 13. Since the pumps operate at synchronous speed, the reagent flow rate is fixed at one half that of the buffer. Samples to be loaded onto the column 15 are injected into conduit 12 and mixed with buffer 11 at sample injector 14. The sample and buffer solution is then eluted through chromatographic column 15 which is itself temperature controlled by water jacket 16. The effluent from column 15 is blended with reagent 17 at mixing tee 18 before passing into capillary coil 20 in heated reactor 22. In reactor 22, color development takes place which is detected as the chromatographic stream flows through photometer 23. The optical absorbance measured by photometer 23 is recorded on recorder 26. In addition, the absorbance data may be operated upon by computing integrator 27.

The effluent stream, prior to passing into waste collector 25, flows through drop detector 24. Drop detector 24 develops a clocking signal, the frequency of which is proportional to the total flow rate of liquid through the reactor and photometer. The clocking signal is fed to flow monitor 28. A flow number, which is the sum of the count signal from voltage controlled oscillator 34, as accumulated during a time determined by the clocking signal, is then compared to a predetermined reference number. The flow number is herein defined as this accumulated count signal. The reference number is selected by the operator to reflect desired system operating parameters. That is, the reference number determines the allowable variation in flow rate before the instrument will be turned off. Under satisfactory operating conditions, the flow number is less than the reference number. Flow monitor 28 continuously compares these two numbers and generates a shutdown signal should a disturbance in flow rate cause the flow number to exceed the preselected reference number. Loss of flow could be caused by running out of buffer or reagent solution, ruptured tubing, leaking fittings, pump failure, etc.

Under proper operation, the flow number will remain essentially constant over a large range of flow rates. The demand for higher flow rates, as generated by the pump drive circuits, produces a higher count signal rate. However, the associated increase in flow reduces the length of counting period because the drops detected by the drop detector come more rapidly. Thus, the same flow number results from more rapid count accumulation over a shorter period of time. Conversely, the count signal associated with lower flow rates will have a lower frequency but, because the output flow or drop rate is also reduced, the clocking period will be proportionately increased. Hence, in a properly operating system, the flow number remains essentially constant and, once the flow number is established, the system remains in calibration over the range of flow rates normally employed.

Referring to FIG. 2, a schematic of pump controlling means 21 is illustrated. A very stable reference voltage 35, which is adjustable by the operator, serves as the flow rate selector. A ten turn potentiometer calibrated in milliliters per hour permits the buffer flow rate to be adjusted over the range of five to fifteen milliliters per hour. Reagent flow rate is fixed at one half of the buffer flow rate. The reference voltage is used to control the frequency of the voltage controlled oscillator 34 and the voltage of power supply 33. The count signal from voltage controlled oscillator 34 passes through gating circuitry 32 to two identical three-phase frequency synthesizers 29 and 31. Synthesizers 29 and 31 drive three-phase pumps 13 and 19, respectively. Because synthesizers 29 and 31 operate from the same oscillator 34, the pump motors operate at synchronous speed.

Logic gate circuitry 32 permits pumps 13 and 19 to be turned on and off as required by programmer circuit 36 during automatic operation of the analyzer. Power supply 33 supplies the driving power for pumps 13 and 19. It is necessary to adjust the voltage level of power supply 33 in relation to the speed at which pumps 13 and 19 are operating. The lower back electromotive force generated by the motors in pumps 13 and 19 at reduced speeds would cause motor winding current to be excessive if the voltage were not reduced. In addition to generating a signal to drive the three-phase frequency synthesizers 29 and 31, voltage controlled oscillator 34 also generates the count signal which is fed to flow monitor 28 (shown in FIG. 1). Thus, a change in the output of oscillator 34 to vary pump speed will also result in a proportional change in the count signal to flow monitor 28.

Flow monitor 28 is shown schematically in FIG. 3. The count signal frequency from voltage controlled oscillator 34 (in FIG. 2) is divided by a factor of 16 in divider counter 37. This divided signal is then accumulated in a seven bit binary counter 38. The counting period for counter 38 is determined by the period between drops passing over drop detector 24. The flow number is then that value accumulated in counter 38 at the end of each counting period. Each drop generates a clocking pulse which resets divider counter 37 and counter 38. For a steady state flow condition, the drops will be equally separated in time, and counter 38 will accumulate essentially the same flow number for each counting period. The five most significant digits in counter 38 are compared in comparator 41 against a five digit number, of which the most significant digit is fixed. The next four digits are selectable by a four bit binary switch 42. If the flow number accumulated in counter 38 exceeds the reference number defined by the fixed digit and that entered into switch 42, then comparator 41 generates an output pulse to preset counter 43.

The reference number entered into switch 42 can be selected such that, under steady state conditions, the flow number accumulated in counter 38 remains less than the reference and no output pulse would be generated from comparator 41. However, if an uncontrolled flow reduction occurs because of a leak or some other system defect, the period between drops will increase. Because the reference frequency remains the same, the count accumulated in counter 38 over the longer period will exceed the reference number and a pulse will be outputted from comparator 41.

Binary switch 42 is the means by which the detector is calibrated. That is, if the reference number is set close to the flow number accumulated in counter 38 under steady state conditions, then it will take less reduction in flow to generate an output pulse than if the reference number is much larger than the steady state flow number accumulated in counter 38. Under normal operation the flow number accumulated in a single timing period will remain essentially constant within the flow rate range of the instrument. This is true because the drop rate varies directly with the pumping speed. For example, as the pump motor speed and thus the count signal is increased by adjusting voltage 35, the drop rate also increases, causing the timing period to be shorter. Essentially the same number of counts are thus accumulated at a faster rate over a shorter period. The relation also holds true if voltage 35 is adjusted to decrease pump motor speed.

The remainder of the flow monitor circuit forms a digital filter to eliminate spurious output signals. This is to ensure that small transient flows due to temporary blockages or other temporary reduction in flow rate will not cause the analyzer to be shut down. The clocking signal from drop detector 24 is divided by three in divider counter 39 such that it will preset counter 43 every three clocking periods. If preset counter 43 receives an output pulse from comparator 41 during each of three successive timing periods, then it will generate an output signal indicating reducing flow thus shutting down the analyzer. At the end of there timing periods, preset counter 43 will again be preset and thereby require counts on each of the next three timing periods in order to indicate a reduced flow.

To disable the flow monitor during transient periods of startup, the output signal from preset counter 43 is passed through gate 44. Gate 44 is disabled if either pump is turned off. It is enabled after both pumps have been operating for a predetermined period of time as determined by time delay 45. The output of gate 44 is then the shutdown signal shown in FIG. 1 and FIG. 3 which would be used to disable the instrument.

For a typical amino acid analyzer in which the invention may be used, the normal buffer flow rate could range from a minimum of 5 milliliters per hour to a maximum of 15 milliliters per hour. The total flow rate from both pumps would then range from a minimum of 7.5 milliliters per hour to 22.5 milliliters per hour. Given these flows, the count signal from voltage controlled oscillator 34 would vary from a minimum of 180 Hz to a maximum 540 Hz. The drop period measured by drop detector 24 varies from a minimum of 1.5 seconds to a maximum of 4.5 seconds. An overall flow rate of 15 milliliters per hour (10 milliliters per hour buffer plus 5 milliliters per hour reagent) coincides with a count signal of 360 Hz, and produces a drop period of approximately three seconds. The flow number accumulated in counter 38 after 3 seconds is then approximately 68 counts (360 Hz times three seconds divided by 16). Even if the flow rate is increased or decreased by adjusting the speed of pumps 13 and 19, the flow number accumulated in counter 38 will remain close to 68 counts.

A decrease in flow due to pump failure, ruptured conduit, etc., will trigger a shutdown. For example, if we assume full loss of reagent flow due to failure of pump 19, then the drop period will increase to about four seconds. The flow number now accumulated in the new counting period will be about 90 (360 Hz times four seconds divided by 16). Thus, to detect a loss of reagent flow, a reference number of 80 could be selected in switch 42. At a steady state condition the flow number would remain about 68, too low to initiate shutdown. If reagent flow stopped, the flow number would rise to 90 which would trip the shutdown. The sensitivity of detection may be increased by setting the reference number closer to 68.

Use of the invention with an instrument allows automatic flow rate adjustment in that a dial calibrated directly in terms of column flow rate is used. Systems now in use require the operator to adjust the flow rates by individually adjusting the pump stroke displacement on each of the pumps, a laborious and time consuming process. In addition, the operation of the flow monitor is completely automatic. That is, once the sensitivity of the detector is set (normally a factory or service adjustment) the detector is in calibration for all flow rates. Existing flow rate detectors require adjustments for each flow rate selected. These adjustments require a certain level of intuitive skill not attained by all operators, thus resulting in malfunctioning of the instruments.

While particular forms of the invention have been disclosed with respect to a preferred embodiment thereof, it is not to be so limited as changes and modifications may be made without departing from the scope of the invention. For example, while the invention has been disclosed as used in a chromatographic instrument, it may be used with any suitable liquid flow instrument. Another possibility is that the count frequency used in the flow monitor could be generated by a separate voltage controlled oscillator for a system in which variable speed motors were not used. This would, however, require that the reference voltage be adjusted each time that the flow rate changed. Drop detectors other than the conductivity probe shown could also be used with the invention. The execution of the digital logic involved in the invention could be accomplished as a software routine in a microprocessor based control system. The inputs to the microprocessor would be the signals from the VCO and the drop detector. The counting, comparing, filtering, etc., would be done within the microprocessor.

While the clocking signal is generated by a drop detector in the preferred embodiment, other generating means may be used. For example, if the effluent from the conduit was a stream rather than drops, a clocking pulse could be generated by any flowmeter which generates a pulse train proportional to the flow rate of the liquid passing therethrough.

The foregoing description, taken together with the appended claims, constitutes a disclosure which enables one skilled in the art and having the benefits of the teachings contained therein to make and use the invention. Further, the structure herein described constitutes a meritorious advance in the art which is unobvious to such skilled workers not having the benefit of these teachings.

What is claimed is:

1. Apparatus employed with a liquid chromatograph instrument, said instrument including a chromatographic column, said device comprising:

means, associated with said column, for pumping a liquid;
    a voltage controlled oscillator cooperative with said pumping means;
    a drop detector associated with said chromatographic column;
    means, adapted to receive a count signal from said voltage controlled oscillator and a clocking signal from said drop detector, for accumulating said count signal from said voltage controlled oscillator during a time determined by said clocking signal from said drop detector; and
    means, responsive to said accumulating means, for comparing said accumulated counting signal with a preselected reference number.

2. Apparatus according to claim 1 wherein said drop detector includes a conductivity probe.

3. Apparatus according to claim 1 wherein said accumulating means includes at least one digital counter.

4. Apparatus according to claim 1 wherein said comparing means includes a digital comparator.

5. A method for monitoring the actual flow rate of a liquid through a liquid chromatography column comprising the steps of:

preselecting a reference number;
    selecting the quantity of said liquid to be pumped into said column;
    pumping said liquid into said column;
    propagating a count signal indicative of the intended pumping flow rate;
    detecting the actual drop flow rate of said liquid after elution through said column;
    generating a clock signal in response to said actual drop flow rate;
    accumulating said count signal for a time determined by said clock signal; and
    comparing said accumulated count signal to said preselected reference number.

* * * * *